US008753313B2

(12) United States Patent
Kimmel et al.

(10) Patent No.: US 8,753,313 B2
(45) Date of Patent: Jun. 17, 2014

(54) INTRODUCER HANDLE NOTCH DESIGN/CONCEPT (75) Inventors: Scott Kimmel, St. Paul, MN (US); Nicholas Kampa, St. Paul, MN (US); Mark Nelson, Plymouth, MN (US); Blane Larson, Monticello, MN (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 13/555,470

(22) Filed: Jul. 23, 2012

(65) Prior Publication Data
US 2014/0025003 A1 Jan. 23, 2014

Related U.S. Application Data (60) Provisional application No. 61/510,510, filed on Jul. 22, 2011.

(51) Int. Cl.
*A61M 5/178* (2006.01)

(52) U.S. Cl.
USPC .............. 604/96.01; 604/164.01; 604/164.05; 604/161

(58) Field of Classification Search
USPC ............. 604/164.01, 164.03, 164.04, 164.05, 604/164.08–164.1; 606/198
See application file for complete search history.

(56) References Cited

U.S. PATENT DOCUMENTS

| | | |
|---|---|---|
| RE31,855 E | 3/1985 | Osborne |
| 4,596,559 A | 6/1986 | Fleischhacker |
| 4,772,266 A | 9/1988 | Groshong |
| D318,733 S | 7/1991 | Wyzgala |
| 5,125,904 A * | 6/1992 | Lee ................................ 604/256 |
| 5,167,634 A * | 12/1992 | Corrigan et al. .............. 604/160 |
| 5,250,033 A | 10/1993 | Evans et al. |
| 5,312,355 A * | 5/1994 | Lee ................................ 604/160 |
| 5,397,311 A * | 3/1995 | Walker et al. ................. 604/160 |
| 5,549,576 A | 8/1996 | Patterson et al. |
| 5,879,333 A * | 3/1999 | Smith ....................... 604/164.04 |
| 5,951,518 A | 9/1999 | Licata et al. |
| D450,839 S | 11/2001 | Junker |
| 6,454,744 B1 | 9/2002 | Spohn et al. |
| 6,692,464 B2 * | 2/2004 | Graf ................................ 604/160 |
| 6,878,134 B2 * | 4/2005 | Rogers et al. ............. 604/164.01 |
| D532,513 S | 11/2006 | Eddings |
| 8,109,908 B1 * | 2/2012 | Kraus et al. ............... 604/164.03 |
| 2002/0128603 A1 * | 9/2002 | Booth et al. .............. 604/164.01 |
| 2005/0010238 A1 * | 1/2005 | Potter et al. .................... 606/129 |
| 2005/0049628 A1 * | 3/2005 | Schweikert et al. .......... 606/198 |
| 2006/0106416 A1 * | 5/2006 | Raymond et al. ............. 606/198 |
| 2009/0192463 A1 * | 7/2009 | Nardeo et al. ............ 604/164.01 |
| 2010/0100044 A1 | 4/2010 | Ye et al. |
| 2011/0264047 A1 | 10/2011 | Kraus et al. |

* cited by examiner

*Primary Examiner* — Quynh-Nhu H Vu
(74) *Attorney, Agent, or Firm* — Steven W. Winn (57) ABSTRACT An improved splittable medical device introducer designed to introduce a medical device such as a lead or catheter, into a patient's vasculature without loss of blood or introduction of air is described. The introducer assembly is designed with a notch provided at the proximal end of the introducer housing. The notch, which may comprise a multitude of cross-sectional geometries, is designed to reduce the force required to separate the housing and the introducer sheath, thereby minimizing the possibility of unintentional dislodgement during separation. The notch also increases the repeatability and consistency of the amount of force required to separate the introducer housing and sheath.

20 Claims, 11 Drawing Sheets

INTRODUCER HANDLE NOTCH DESIGN/CONCEPT

CROSS REFERENCE TO RELATED APPLICATIONS

This application claims priority to U.S. provisional application Ser. No. 61/510,510, filed on Jul. 22, 2011.

BACKGROUND OF THE INVENTION

1. Field of the Invention

The present invention generally relates to introducers and introducing assemblies. Specifically, the present invention is directed to a splittable introducer with a notched housing.

2. Prior Art

Introducer devices provide for access to the venous system and are employed for inserting medical devices such as catheters, guidewires, leads, infusion ports, dialysis ports, dialysis catheters, and others. A typical procedure for gaining access to the central venous system or the arterial system with an introducer is the Seldinger Introduction Method. The Seldinger Method provides for insertion of a needle into the vasculature of a patient. Once the needle is in the vessel, the physician aspirates the needle with a syringe to assure that the needle is in the vessel, and to draw out air present in the bore of the needle. The syringe is removed and discarded. A guide wire is inserted through the needle, and the needle is removed over the guide wire. The introducer, which includes a dilator and a sheath, is placed over the guidewire and inserted into the vessel. With the introducer and wire guide in the vessel, the dilator and wire guide are removed leaving only the sheath in the vessel. The desired medical device is implanted through the passage of the sheath. The sheath is optionally removed from the medical device.

The standard method for accomplishing sheath housing separation is by a mechanical breaking or cracking of the sheath housing in two halves. However, there are problems associated with this method.

First, the force required to initiate sheath housing separation for prior art introducers is relatively high. The application of such a required force may not be possible due to the varying physical strengths of care providers. Furthermore, exerting such an increased amount of force on the introducer device may result in the unintentional movement or dislodgement of the device within the vasculature.

Second, the housing of prior art introducers requires a thin wall thickness. This thin wall thickness is necessitated to promote the initiation and propagation of the crack required to separate the housing. However, the addition of desirable ergonometric and aesthetic features increase the thickness and complexity of the housing, thereby increasing the difficulty and force needed to separate the housing. In addition, such complexities are difficult to manufacture and produce such that the housing consistently splits apart with the application of a repeatable and consistent force.

Therefore, what is desired is an introducer device comprising a housing that separates at a reduced force to initiate subsequent splitting or separation of the sheath. In addition, an introducer housing that repeatably and consistently separates upon the application of a consistent separation force is desired. Furthermore, an introducer assembly that is able to be manufactured more easily and consistently is desired.

SUMMARY OF THE INVENTION

An introducer assembly comprising a notched housing is provided herein. The introducer includes a sheath having a sheath proximal end spaced from a distal end, and a sheath lumen that extends longitudinally therethrough. In addition, the introducer assembly of the present invention comprises a dilator subassembly. The dilator subassembly comprises a dilator sheath having a dilator sheath proximal end spaced from a dilator sheath distal end. The dilator is designed such that the dilator sheath is inserted through the lumen of the introducer sheath.

The introducer assembly further comprises a housing subassembly that is positioned over the proximal end of the sheath. The housing subassembly comprises a housing body having a housing body proximal end spaced from a housing body distal end. A housing through-bore extends longitudinally therethrough. A score-line residing within a portion of the thickness of the exterior surface of the housing extends from the housing body proximal end to the housing body distal end.

Positioned at the proximal end of the housing body is a notch that extends at least part way through the thickness of the sidewall and extends from the proximal end of the housing body. This notch, which can comprise a multitude of geometric shapes, is design to concentrate application of the separation force to a specific area or point thus reducing the force required to initiate and propagate the separation crack through the sidewall of the housing body for separating the housing in two.

In addition, a retainer ring may be provided. The retainer ring is designed to act as a temporary valve to prevent the flow of fluids, gas and liquid, through the notch of the housing body. The ring is positioned within or adjacent the through-bore at the proximal end of the housing body. A tab extending from the perimeter wall of the ring is positioned within the opening of the notch to thereby prevent potential fluid flow therethrough.

Advantageously, the introducer assembly described above provides many benefits. For example, the introducer assembly allows for a removable introducer assembly to seal against instruments such as leads or other instruments and devices. These and other embodiments, aspects, advantages, and features of the present invention will be set forth in part in the description which follows, and in part will become apparent to those skilled in the art by reference to the following description of the invention and referenced drawings. The aspects, advantages, and features of the invention are realized and attained by means of the instrumentalities, procedures, and combinations particularly pointed out in the appended claims and their equivalents.

DETAILED DESCRIPTION OF THE PREFERRED EMBODIMENT

Figure 1:
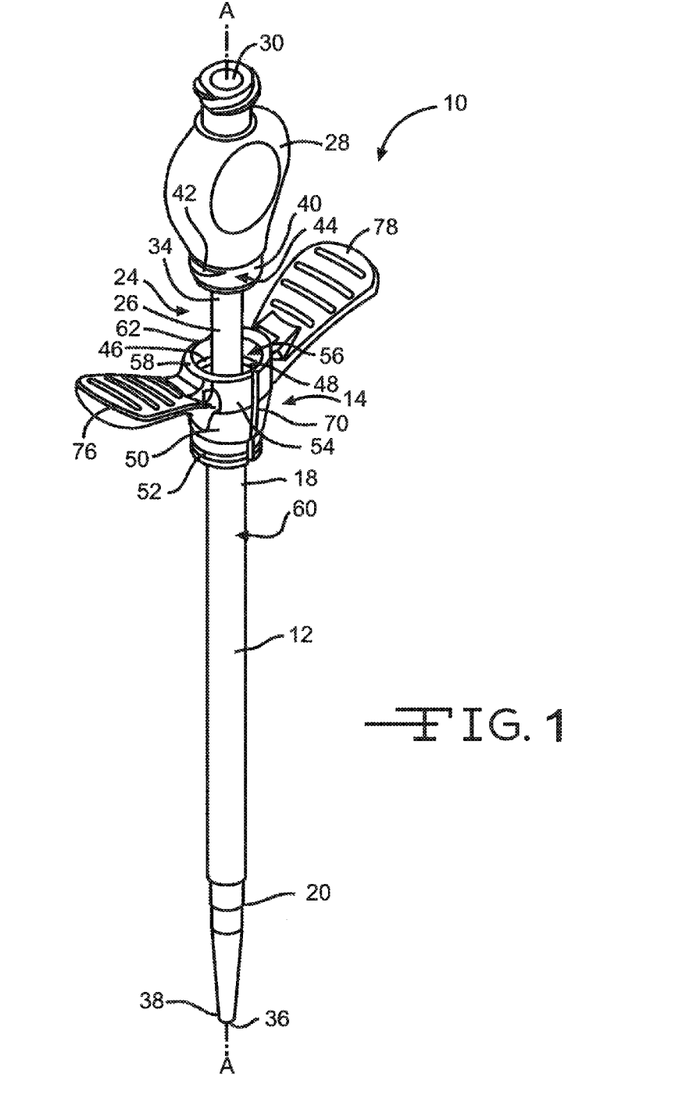
FIG. 1 illustrates a perspective view of an embodiment of an introducer assembly device of the present invention.
Figure 1A:
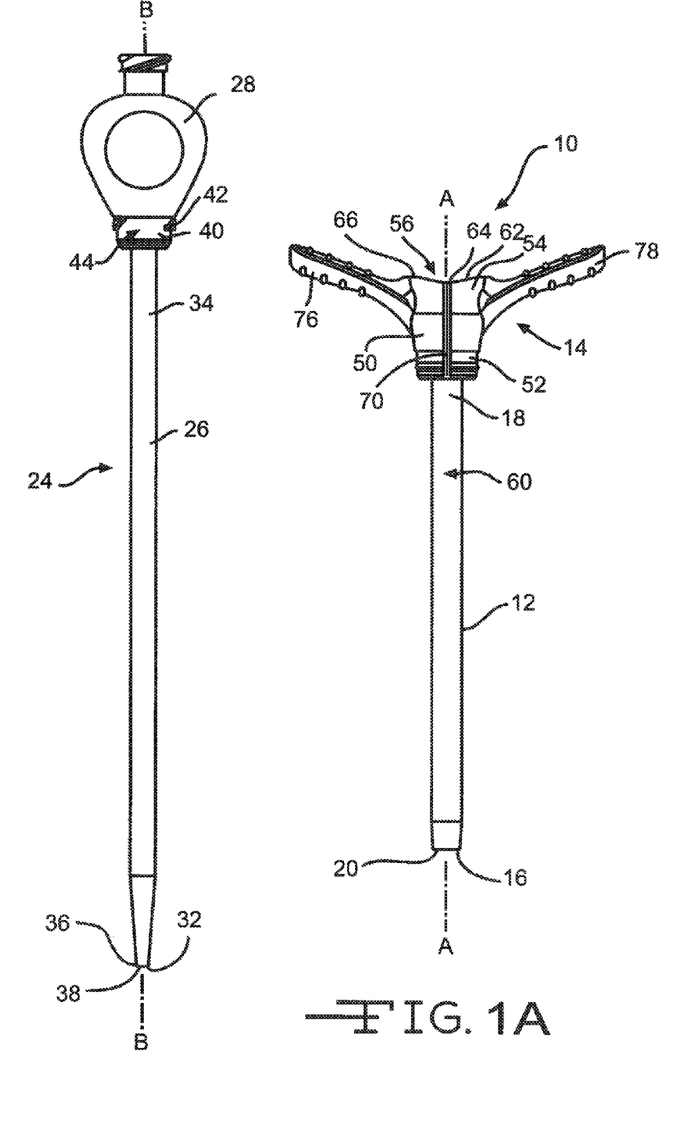
FIG. 1A shows a perspective view of the components comprising the introducer assembly shown in FIG. 1.

Now referring to the figures, FIGS. 1 and 1A illustrate an embodiment of an introducer assembly 10 of the present invention. The introducer assembly 10 comprises an elongated introducer sheath 12 connected to an introducer housing subassembly 14. The sheath 12 is an elongate member having an introducer sheath sidewall 16 extending along a longitudinal axis A-A from a sheath proximal portion 18 to a sheath distal end 20. The thickness of the sidewall 16 including the proximal section 18 extending to the distal end 20 is from about 0.001 inches to about 0.050 inches.

A lumen or passage 22 provides for open communication along the entire length of the sheath 12 and into the introducer housing subassembly 14. This lumen 22 allows for a medical device, such as a lead or catheter, to be advanced through the assembly 10. The lumen 22 preferably has a diameter from about 0.05 inches to about 0.50 inches.

In addition, as shown in FIGS. 1 and 1A, the introducer assembly 10 of the present invention comprises a dilator subassembly 24. As shown, the dilator subassembly 24 comprises an elongated dilator sheath 26 connected to a bulbous dilator head 28. The dilator head 28 comprises a dilator head through-bore 30 which extends longitudinally through the length of the dilator head 28. The dilator sheath 26 is an elongate member having a dilator sheath sidewall 32 extending along a longitudinal axis B-B from a dilator sheath proximal portion 34 to a dilator sheath distal end 36. The thickness of the dilator sheath sidewall 32, including the proximal section 34 extending to the distal end 36, is from about 0.001 inches to about 0.050 inches. The diameter of the distal end 36 of the dilator sheath 26 may be narrow than the diameter of the proximal end portion 34 of the dilator sheath 26. As shown, the distal end 36 of the dilator sheath 26 may comprise a pointed end 38.

The dilator sheath 26 is designed such that it may be inserted within the introducer sheath lumen 22 and extends longitudinally along axis A-A. As shown, the dilator head 28 mates with the housing subassembly 14. In a preferred embodiment, a proximal portion 40 of the dilator head 28 comprises a helical ridge or thread 42 positioned along an exterior surface 44 of the dilator head 28. The helical ridge 42 is designed to threadingly engage within a corresponding groove 46 residing within an interior surface 48 of the housing subassembly 14. When the dilator 24 is positioned within the lumen 22 of the sheath 12, the dilator head 28 is rotated to threadingly engage the helical ridge 42 within the groove 46 of the housing subassembly 14 forming a secure fit therebetween. The dilator 24 may be removed from the sheath 12 by reversing the rotation of the dilator head 28 and removing the dilator from the sheath 12 of the introducer 10.

The housing subassembly 14 comprises a housing body 50 having a housing base portion 52 that fluidly extends to an upper housing web portion 54. As shown, a housing through-bore 56, defining a housing sidewall 58, extends longitudinally along axis A-A. A portion of the sheath proximal region 18 is supported within the through-bore 56 of the housing subassembly 14. More specifically, the portion of the sheath proximal region 18 is designed to be positioned within the through-bore opening 56 of the housing 50, such that the opening of the lumen 22 and the housing through-bore 56 are aligned. In a preferred embodiment, the base portion 52 of the housing body 50 circumferentially extends around an exterior surface 60 of the introducer sheath 12 forming a tight interference fit therebetween. In a preferred embodiment, the base portion 52 of the housing body 50 may be molded over the proximal end portion 18 of the sheath 12.

Figure 3:
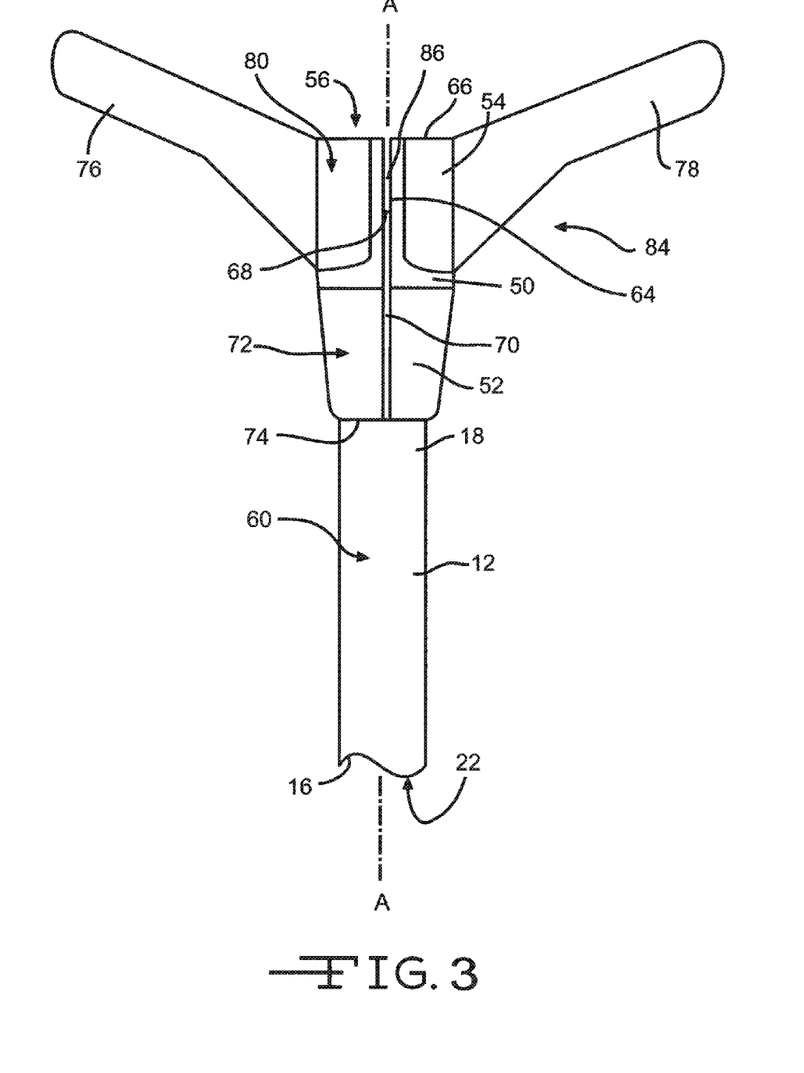
FIG. 3 shows a side view of an embodiment of an introducer housing subassembly comprising a notch stress confining feature of the present invention.

Residing within the upper web portion 54 of the housing body 50 is a stress confining feature 62. More specifically, the stress confining feature comprises a notch 64 that extends from a proximal end 66 of the upper web portion 54 of the housing body 50 to a stress concentration area or point 68 (FIGS. 3 to 5), distal of the proximal end 66. The notch 64 preferably extends through at least a portion of the thickness of the housing body sidewall 58. Alternatively, as shown in the embodiment of FIG. 3, the notch 64 may extend through the entire thickness of the sidewall 58 of the web portion 54 of the housing 50.

A score-line 70 extends distally from the stress concentration area or point 68 of the stress concentration notch 64. The score-line 70 preferably resides within a portion of an exterior surface 72 of the housing body 50. In a preferred embodiment, the score-line 70 extends from the stress concentration point 68 of the notch 64 to a distal end 74 of the base portion 52 of the housing 50. As will be shown in the following examples and illustrations, the housing subassembly 14 of the introducer assembly 10 of the present invention may comprise a multitude of non-limiting notch geometries.

In addition, extending from the housing body 50, are spaced apart wings 76 and 78, which give the housing body 50 a butterfly appearance. More specifically, the opposing left and right wings 76, 78 fluidly extend from an exterior surface 80 of the upper web portion 54 of the housing body 50. These wings 76, 78 are designed such that when a downward and counter rotated force is applied to them, a separation force is thereby applied to the stress concentration feature 62 or notch 64 of the housing body 50. The notch 64 then focuses the separation force to the stress concentration point 68 were a housing separation crack is initiated. Upon the application of an additional opposed lateral pulling force, the initiated crack propagates along the score-line 70 thereby separating the housing subassembly 14 and introducer sheath 12.

Figure 2:
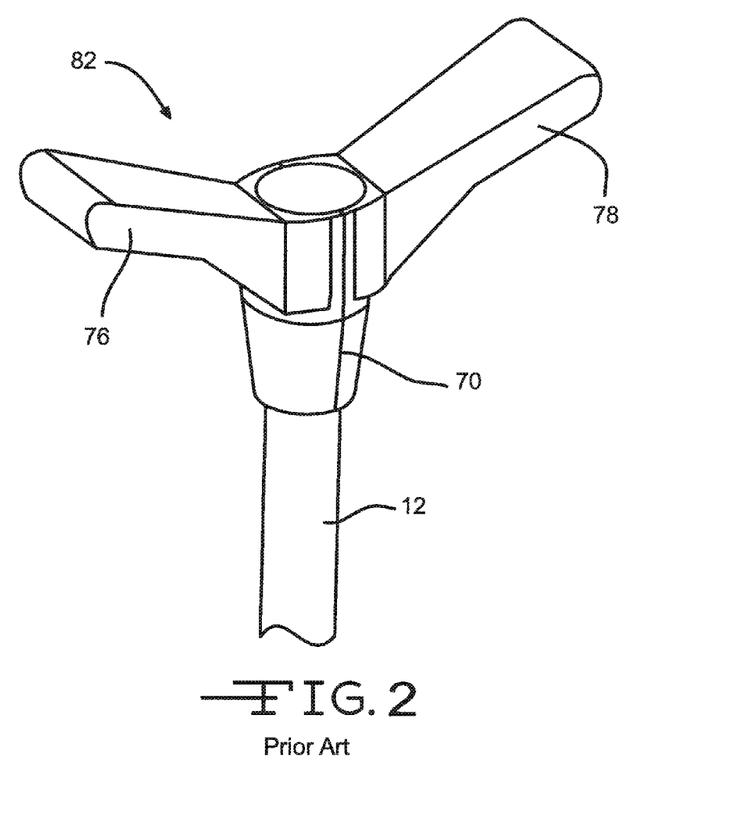
FIG. 2 illustrates a perspective view of a prior art introducer housing subassembly.

In contrast, an embodiment of a housing subassembly 82 of the prior art, as shown in FIG. 2, does not comprise such a stress confining feature or notch. As shown, the prior art housing 82 comprises only the score-line 70 that extends longitudinally from its proximal portion to the distal portion of the housing 82. The lack of such a stress confining feature 62 such as the present notch 64 means that a relatively greater force is required to separate the prior art housing 82 to initiate subsequent splitting separation of the sheath 12.

Figure 3A:
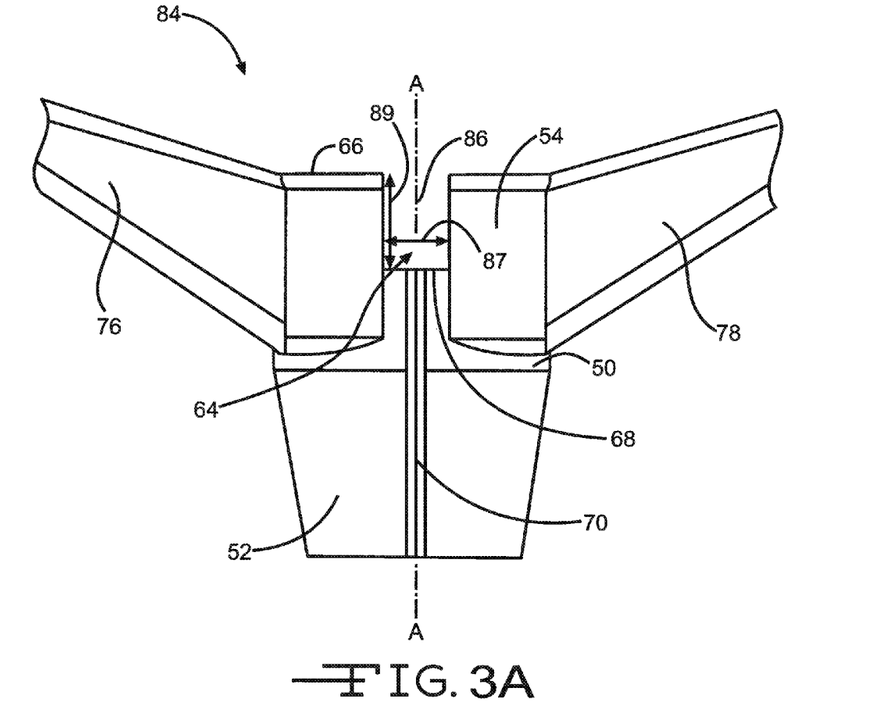
FIG. 3A illustrates a magnified view of the embodiment of the notch stress confining feature shown in FIG. 3.

FIGS. 3, 3A, 4 and 5 illustrate preferred embodiments of introducer housing subassemblies. Specifically, FIGS. 3, 3A, 4 and 5 show preferred embodiments of various stress confining features 62 of the present invention. In particular, FIGS. 3 and 3A illustrate an embodiment of an introducer housing subassembly 84 comprising a notch 86 having a rectangular cross-section. As shown, the notch 86 is formed by removing a portion of the thickness of the sidewall 58 of the upper web portion 54 of the housing 84. More specifically, as shown in FIG. 3A, the notch 86 comprises a notch width 87, a notch length 89, and a notch depth. In a preferred embodiment, the notch width 87 may range from about 0.01 inches to about 0.25 inches, the notch length 89 may range from about 0.01 inches to about 0.25 inches, and the notch depth may also range from about 0.01 inches to about 0.25 inches. In a preferred embodiment, the width of the notch 86 may be greater than the width of the prior art score-line 70 (FIG. 2). The length of the notch 86 may also range from about 5% to about 50% of the length of the upper web portion 54 of the hosing body 50. Furthermore, the depth of the notch 86 may be about equal to the thickness of the sidewall 58 of the housing 50, particularly the sidewall thickness of the upper web portion 54 of the housing 50.

Figure 4:
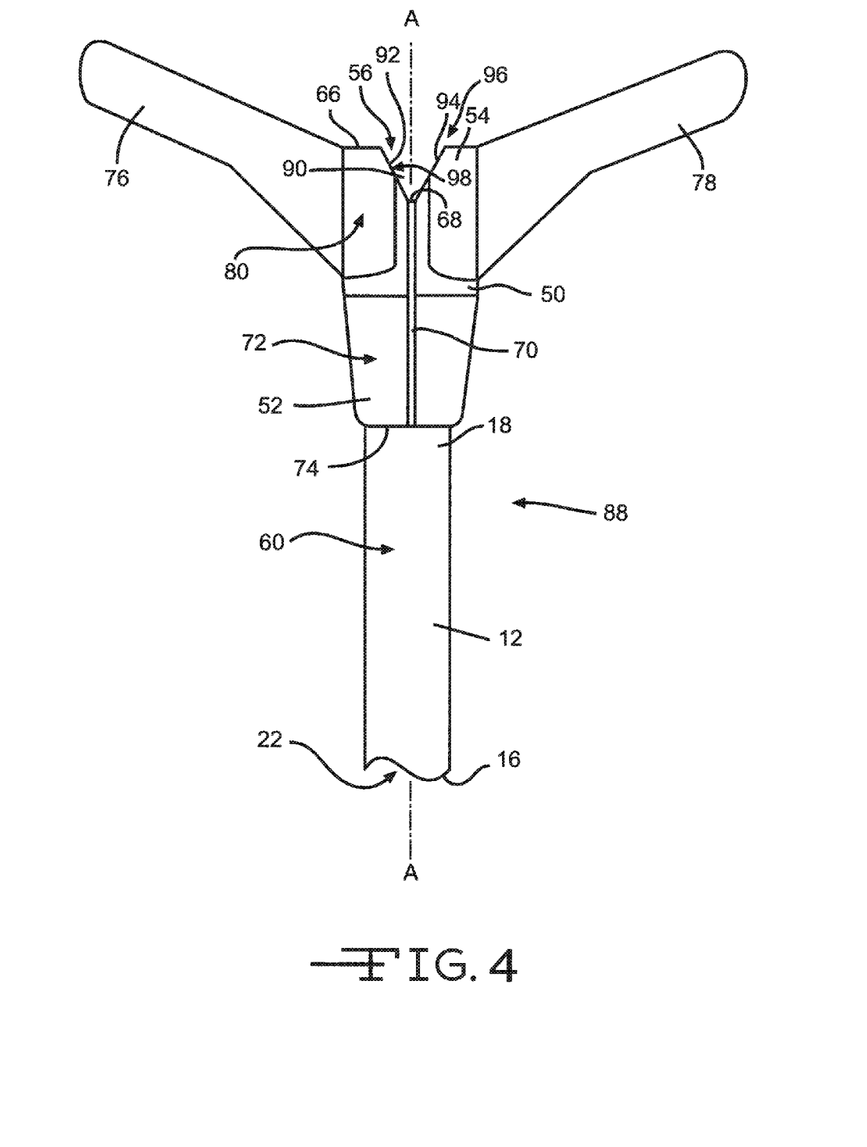
FIG. 4 shows a side view of an introducer housing subassembly comprising an alternate embodiment of a stress confining feature of the present invention.

FIG. 4 illustrates an alternate embodiment of an introducer housing subassembly 88 comprising a notch 90 having a "V" or wedge-like cross-section. As shown this notch 90 comprises a first notch sidewall 92 and a second notch sidewall 94 that converge at the stress concentration point 68. In a preferred embodiment, each of the first and second sidewalls 92, 94 has a notch angle 96 that ranges from about 5° to about 90°. The notch angle 96 is defined as the angle between longitudinal axis A-A and a surface 98 of the notch sidewall 92, 94. The first or second notch sidewalls 92, 94 may have a similar or different notch angle 96. The notch also comprises a notch depth that approximates the thickness of the sidewall 58 of the web portion 54 of the housing body 50.

Figure 5:
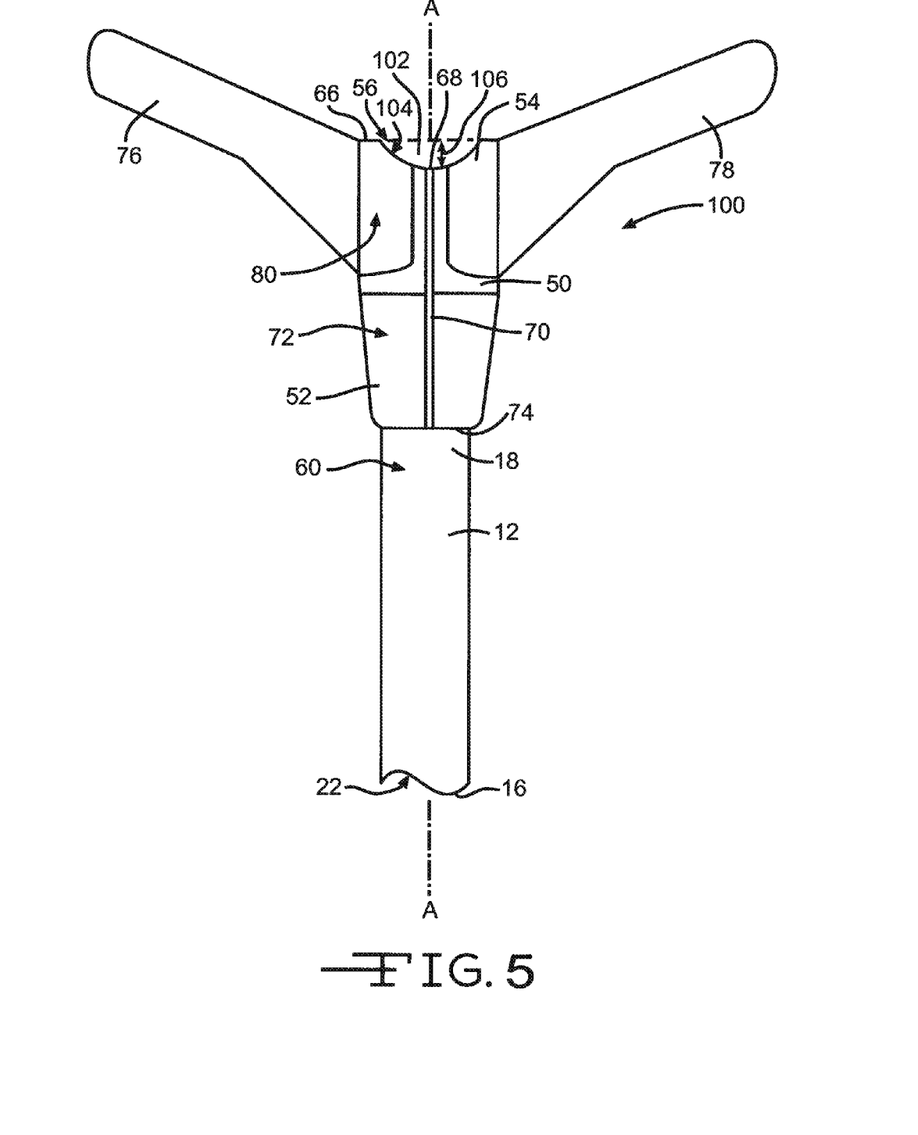
FIG. 5 shows a side view of an introducer housing subassembly comprising an alternate embodiment of a stress confining feature of the present invention.

FIG. 5 illustrates yet another alternate embodiment of an introducer housing subassembly 100 comprising a notch 102 having a curved cross-section. As shown, the notch 102 comprises a curved surface 104 that resides within a portion of the thickness of the sidewall 58 of the housing body 50. In a preferred embodiment, the curved surface of the notch has a notch radius of curvature that ranges from about 0.1 inches to about 0.25 inches.

The notch 102 comprises a notch depth 106 that penetrates through a portion of the length of the web portion 54 of the housing 50. As shown, the notch depth extends from the proximal housing end 66 of the upper web portion 54 to a point distal of the proximal end 66. In a preferred embodiment, the notch depth 106 may range from about 0.01 inches to about 0.25 inches. Alternatively, the notch depth 106 may range from about 5 percent to about 25 percent of the length of the web portion 54. The notch also comprises a notch width that may span about the thickness of the sidewall of the upper web portion 54.

TEST DATA

A series of mechanical tests were performed comparing the measured separation force of the introducer assembly 10 of the present invention to that of the force required to separate the housing 82 of the prior art (FIG. 2). Specifically, introducer assemblies 10 comprising the curved notch housing subassembly embodiment 100 (FIG. 5) were tested against the housing 82 of the prior art introducer assembly illustrated in FIG. 2.

Table I, shown below, summarizes the mechanical test data of the introducer assembly of the prior art. As shown, the average measured forces required to separate the housing 82, of various introducer diameters, i.e., French sizes, of the prior art design are detailed below in Table I. During the test, separation forces were measured and averaged for a total of 10 introducer samples per French size, sizes 7 French to 17 French in total. The French size scale is commonly used in the medical device arts to denote the diameter of a lead or a catheter. A French size of 1 equates to a diameter of about 0.33 mm.

TABLE I

| | Dia. | | | | | | | | | | |
|---|---|---|---|---|---|---|---|---|---|---|---|
| | 7 Fr | 8 Fr | 9 Fr | 10 Fr | 11 Fr | 12 Fr | 13 Fr | 14 Fr | 15 Fr | 16 Fr | 17 Fr |
| Avg. Force (lbs-f) | 14.8 | 18.0 | 17.2 | 17.5 | 15.1 | 14.2 | 16.2 | 17.6 | 17.8 | 19.0 | 16.6 |
| Std. Dev. | 0.5 | 0.2 | 0.3 | 0.4 | 0.4 | 0.3 | 1.5 | 0.9 | 0.4 | 0.9 | 0.5 |
| Cpk | 3.6 | 4.6 | 2.8 | 1.9 | 4.7 | 5.9 | 0.8 | 0.9 | 1.7 | 0.4 | 2.5 |

Table II, shown below, summarizes the mechanical test data of the force required to separate the housing subassembly 100 of the present invention among various French sizes. More specially, separation forces were measured and averaged on a total of 10 introducer samples per French size, sizes 7 French to 17 French in total. The test samples comprised the curved notch feature embodied in FIG. 5.

TABLE II

| | Dia. | | | | | | | | | | |
|---|---|---|---|---|---|---|---|---|---|---|---|
| | 7 Fr | 8 Fr | 9 Fr | 10 Fr | 11 Fr | 12 Fr | 13 Fr | 14 Fr | 15 Fr | 16 Fr | 17 Fr |
| Avg. Force (lbs-f) | 11.4 | 13.6 | 13.6 | 13.2 | 10.6 | 9.8 | 11.4 | 13.2 | 14.0 | 14.9 | 12.7 |
| Std. Dev. | 0.4 | 0.4 | 0.3 | 0.3 | 0.4 | 0.2 | 0.4 | 0.6 | 0.8 | 0.6 | 0.6 |
| Cpk | 6.6 | 5.0 | 6.2 | 9.0 | 7.2 | 16.4 | 7.5 | 4.0 | 2.4 | 2.9 | 4.3 |

As can be seen from the test data, the overall average force required to separate the notched housing 100 of the introducer assembly 10 of the present invention was less than the average force required to separate the housing 82 of introducer assembly of the prior art. The test data therefore, illustrates a direct reduction in the separation force of the introducer assembly 10 of the present invention comprising the notched housing 100.

In addition, the increased process capability index values (Cpk) resulting from the testing of the introducer design of the present invention, as shown in Table II, illustrate the increased repeatability of the force required to separate the test samples. Process capability index is herein defined as a statistical measure of process control. The greater the Cpk value, the greater the repeatability and control the process, or in this case, the measured separation force values.

TABLE III

| | Dia. | | | | | | | | | | |
|---|---|---|---|---|---|---|---|---|---|---|---|
| | 7 Fr | 8 Fr | 9 Fr | 10 Fr | 11 Fr | 12 Fr | 13 Fr | 14 Fr | 15 Fr | 16 Fr | 17 Fr |
| Percent Diff. | 22.5 | 24.2 | 20.6 | 24.4 | 29.9 | 30.8 | 29.7 | 25.1 | 21.1 | 21.5 | 23.3 |

Table III details the percent difference in the average measured forces required to separate the respective housing subassemblies. As shown, the average force required to separate the housing assembly 82 of the prior art design was greater for every diameter size. For example, the force required to separate a 10 French diameter prior art introducer assembly measured, on average, about 17.5 lb-force. In comparison, the average force required to separate the housing 100 of the introducer assembly 10 of the present invention comprising the curved notch 102 measured about 13.2 lb-force. This, as shown in Table III, corresponds to a reduction in separation force of about 24.4 percent. Therefore, as can be seen from the test data above, the force required to separate the notched introducer assembly of the present invention is not only less than the force required to separate the introducer assembly of the prior art but also exhibits greater consistency and repeatability.

Figure 6:
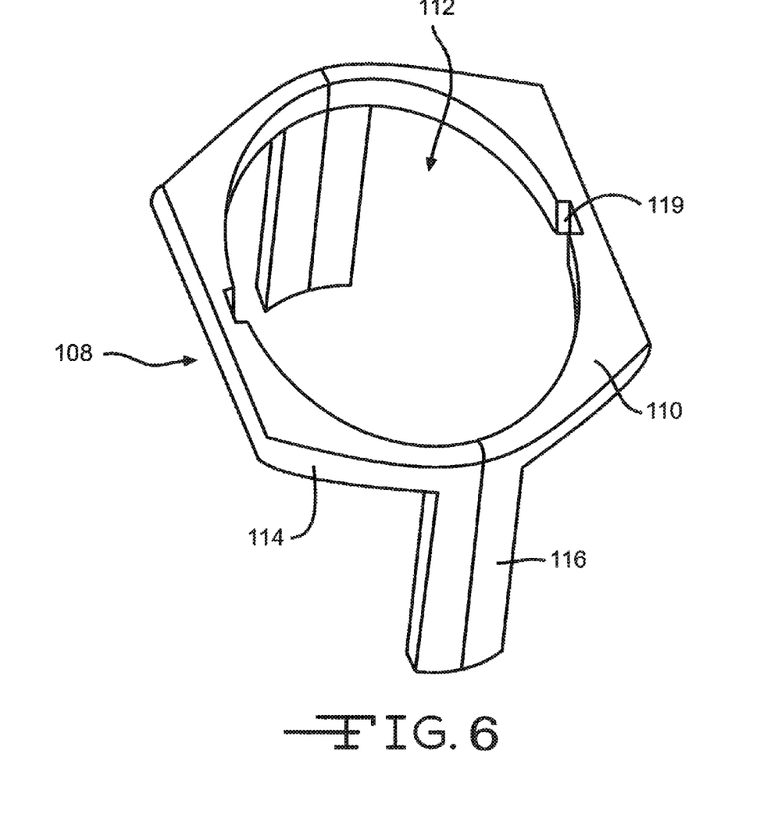
FIG. 6 illustrates an embodiment of a retainer ring of the present invention.
Figure 7:
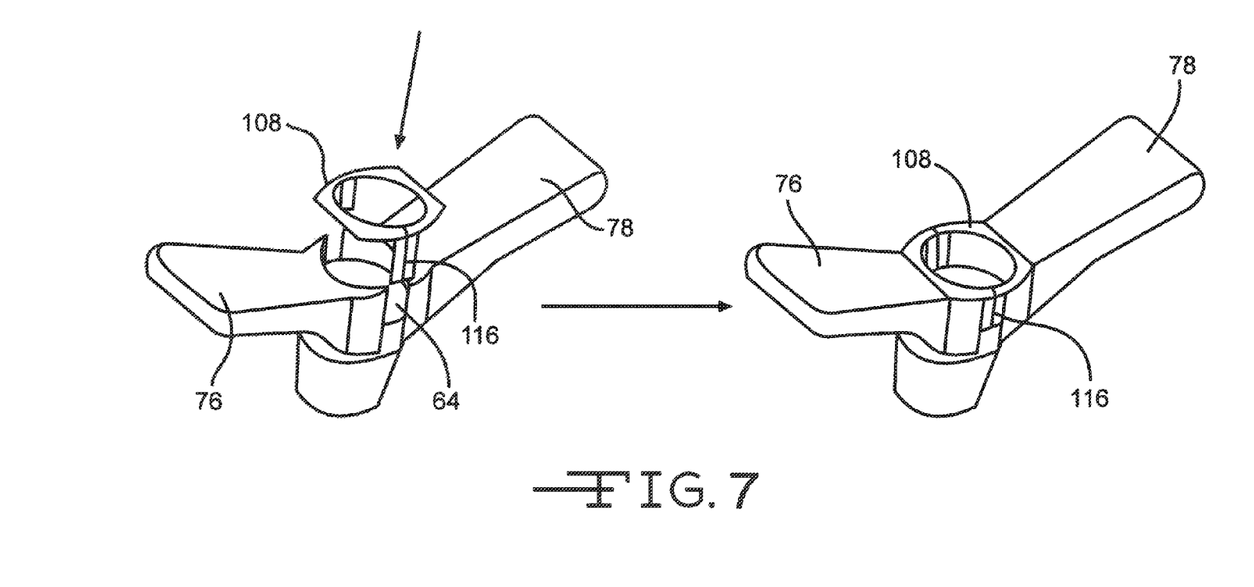
FIG. 7 illustrates the embodiment of the retainer ring of FIG. 6 being positioned within the introducer assembly of the present invention.
Figure 7A:
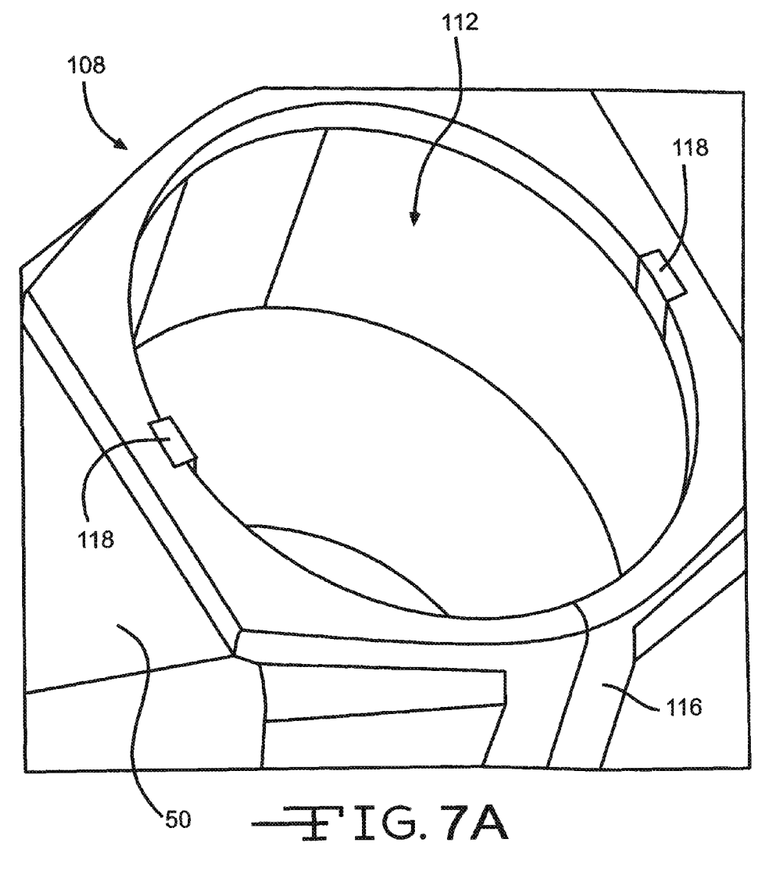
FIG. 7A shows a magnified view of the retainer ring, shown in FIG. 6, positioned within the introducer assembly.

FIGS. 6, 7 and 7A, illustrate an embodiment of a retainer ring 108. The retainer ring 108 may be used with the introducer assembly 10 of the present invention as a means to prevent the possible flow of fluids such as a gas or liquid through the opening of the notch 64. The ring 108 is designed to be either placed adjacent to or inserted within the proximal end 66 of the housing subassembly 14. As shown, the retainer ring 108 comprises an annular retainer body 110 in which a retainer through-bore 112 extends. Extending from a perimeter sidewall 114 of the ring 108 is a tab 116 that is designed to be inserted within the notch 64 of the housing body 50. In a preferred embodiment, at least two opposing tabs 116 project from the perimeter sidewall 114 of the retainer ring 108. The tab or tabs 116 are dimensioned to fit within the opening of the notch 64. In a preferred embodiment, the tab 116 is of a rectangular cross-section however, the tab 116 may comprise a cross-sectional dimension such that the tab 116 fits within the various embodiments of the notches.

As shown in FIG. 7, the retainer ring 108 maybe positioned over or within the through-bore opening of the proximal end 66 of the housing subassembly 14. A clip 118 portion of the housing body 50, as shown in FIG. 7A, may be used to hold the retainer ring 108 in place within or over the through-bore 56 of the proximal end 66 of the housing subassembly 14. The clip 118 is positioned within a recess 119 of the perimeter sidewall 114 of the retainer ring 108 (FIG. 6). The clips 118 are diametrically opposite to each other and preferably offset 45° from the tabs 116.

Figure 8:
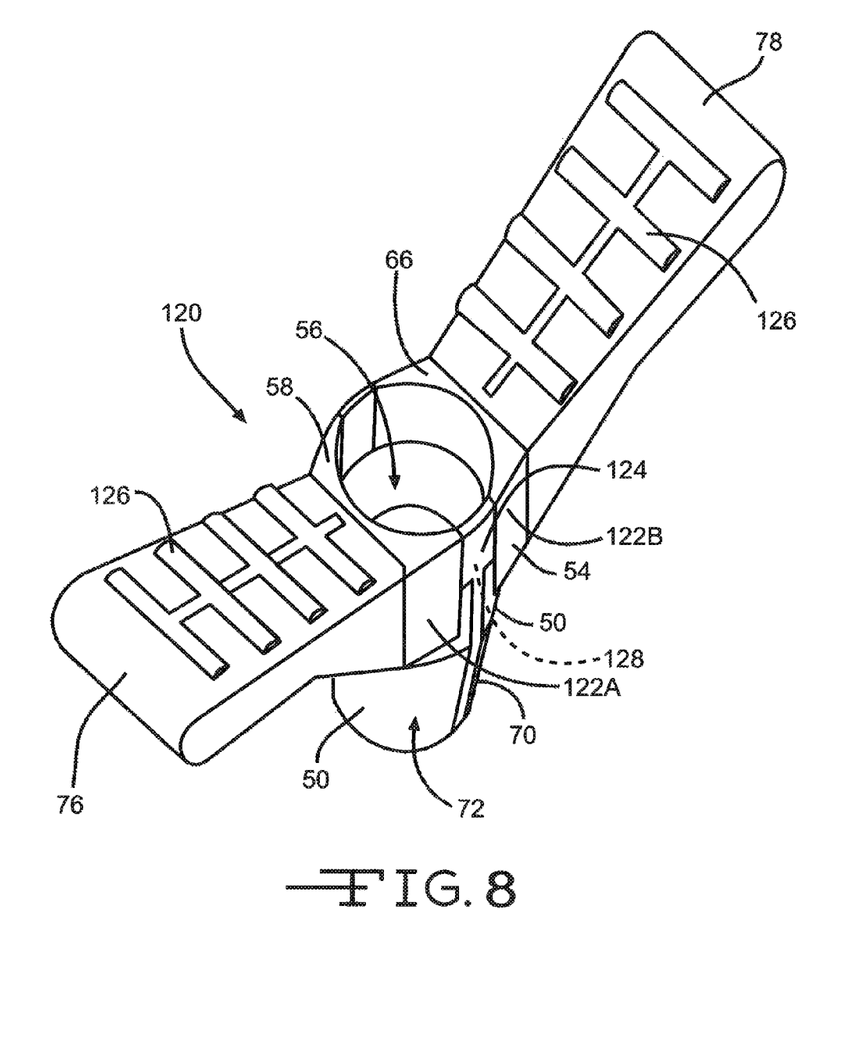
FIG. 8 illustrates an embodiment of the housing subassembly comprising a break-away flap feature.

FIG. 8 illustrates yet another alternate embodiment of a housing subassembly 120 of the present invention. Similar to the previous embodiments of the housing subassemblies, this embodiment comprises a housing body 122 having opposing left and right wings 76, 78 that extend from the exterior surface 72 of the body 122. Similar to the previous housing subassemblies of the present invention, the score-line 70 resides within a portion of the thickness of the exterior surface 72 extending from the upper web portion 54 to the distal base portion 52 of the housing 120. The central throughbore 56 extends therethrough.

However, unlike the previous embodiments of the housing subassemblies, this embodiment 120 comprises a flap 124 that is designed to break away when a force is applied to the left and right wings 76, 78. Furthermore, the housing subassembly 120 comprises a series of raised ridges 126 residing within the left and right wings 76, 78. These ridges 126 are designed to add strength and rigidity to the wings 76, 78.

In an embodiment, the flap 124 is connected between the opposing left and right wings 76, 78 of the housing subassembly 120, such as by molding. More specifically, as shown in FIG. 8, the flap 124 is positioned and connected between respective left and right sides 122A, 122B of the upper housing portion 54. Each flap 124 resides within a corresponding notch 128 within the sidewall 58 of the housing upper portion 54 of the housing subassembly 120. In an embodiment, each flap 124 may be composed of a rigid polymeric material that easily breaks under a mechanical stress. In addition, the flap 124 may be composed of santoprene, silicone, polyether block amides and the like.

When a force is applied to the opposing left and right wings 76, 78 the flap 124 breaks off, of the left and right side 122A, 122B of the upper housing portion 54, thereby exposing the notch 64 positioned within the sidewall 58 of the housing body 122. Thus, when the flap 124 breaks off, the notch 128 concentrates application of the separation force to the score-line 70, thereby initiating a separation crack therebetween.

In operation, the dilator 24 is received inside the lumen 22 of the introducer sheath 12. This allows for the introducer assembly to be introduced into the vasculature of a patient, for instance, over a guide wire (not shown). This positions the distal end 20 of the sheath 12 inside the vasculature while the proximal section 18 and the housing subassembly 14 remain outside the patient. After the introducer assembly 10 is inserted into a patient and the dilator has been removed from the sheath 12, other medical instruments can be easily inserted into and through the sheath 12 and introduced into the patient. The retainer ring 108 may be positioned within the through-bore 56 of the housing subassembly 14 at its proximal end 66 to prevent blood and other body fluids from leaking out of the vasculature and outside air from getting in.

Then, once the lead or catheter is properly positioned in the vasculature, the introducer assembly 10 of the present invention is split apart for removal from the vasculature. This is done by holding the wings 76, 78 between the thumb and fore finger and counter rotating them with respect to each other while slowly moving the wings further apart. The housing body 50 is readily separated. This occurs at the score-line 70 that runs along the base portion 52 of the housing body 50.

As the wings 76, 78 of the housing 50 are moved apart, the resulting halves of the housing begin to exert a force on the proximal end 18 of the sheath 12. These forces are concentrated at the notch 64, particularly at the stress concentration point 68 to initiate a tear at the proximal end of the score-line 70. The force generated by further manipulation of the wings 76, 78 is concentrated at the lower extent or distal stress point/area 68 of each notch feature 64. This concentrated force is sufficient to cause the material of the housing subassembly 14 to sever or tear apart from the sheath 12.

The housing subassembly 14 of the present invention is preferably composed of an acrylic based polymeratial, such as polymethyl methacrylate. In addition, the housing subassembly 14 may also be composed of ethyl acrylate, 2-chloroethyl vinyl ether, 2-ethylhexyl acrylate, hydroxyethyl methacrylate, butyl acrylate, butyl methacrylate and the like.

The sheath 12 of the present invention preferably comprises polytetrafluoroethylene (PTFE). While PTFE is the most preferred material for the housing 14, other fluoropolymeric materials may also be used. These include polyhexafluoropropylene, tetrafluoroethylene-hexafluoropropylene copolymers, tetrafluoroethylene-perfluoroalkyl vinyl ether copolymers, polytrifluoroethylene, ethylene-tetrafluoroethylene copolymers, fluoroethylene-hydrocarbon vinyl ether copolymers, polychlorotrifluoroethylene, ethylene-chlorotrifluoroethylene copolymers, polyvinyl fluoride, polyvinylidene fluoride, vinylidene fluoride-hexafluoropropylene copolymers, fluorinated (meth)acrylate resins, 2-fluoroacrylate resins, fluorinated epoxy resins, fluorinated epoxy (meth)acrylate resins, fluorinated polyether resins, fluorinated polyimide resins, fluorinated polyester resins, fluorinated polyamide resins, fluorinated polycarbonate resins, fluorinated polyformal resins, fluorinated polyketone resins, fluorinated polyazomethine resins, fluorinated polyazole resins, and fluorinated polyallyloxysilane resins, vinylidene fluoride-hexafluoropropylene fluoroelastomer, vinylidene fluoride-tetrafluoroethylene fluoroelastomer, tetrafluoroethylene-perfluoroalkyl vinyl ether fluoroelastomer, vinylidene fluoride-tetrafluoroethylene-hexafluoropropylene fluoroelastomer, vinylidene fluoride-tetrafluoroethylene-perfluoroalkyl vinyl ether fluoroelastomer, tetrafluoroethylene-perfluoroalkyl vinyl ether fluoroelastomer, propylene-tetrafluoroethylene fluoroelastomer, fluorosilicone rubber, fluorinated phosphazene rubber, fluorinated thermoplastic rubbers, and flexible fluorocarbon resins.

The present invention thus provides the upper web portion 54 of the introducer 10 with structures that concentrate the tearing forces created by moving the wings 76, 78 apart to stress confining features 62 located diametrically opposite each other in the housing sidewall 58. However, the present invention is not meant to be limited to the notch embodiments discussed and illustrated. Any structure located at the upper web portion 54 of the housing body 50 that serves to concentrate the tearing forces to a confined area is contemplated by the scope of the present invention.

Thus, the present invention has described several structures suitable as stress confining structures for concentrating the separating forces exerted at the upper web portion 54 of the housing body 50 by a pulling manipulation of the wings 76, 78. In each structure, the total forces imparted to the wings 76, 78 are concentrated at either diametrically opposed surfaces along the proximal end 66 of the upper web portion 54. Together with the unique molecular properties afforded by PTFE as the preferred material for the sheath 12, once a tear begins it propagates the entire length of the sheath, no matter how long, in an extremely smooth manner that provides the physician with a very desirable tactile feel.

It is, therefore, apparent that there has been provided, in accordance with the present invention, an introducer assembly comprising a housing supported on the proximal end of a sheath having a novel structure for removal from the venous system of a patient. While this invention has been described in conjunction with preferred embodiments thereof, it is evident that many alternatives, modifications, and variations will be apparent to those skilled in the art. Accordingly, it is intended to embrace all such alternatives, modifications and variations that fall within the broad scope of the appended claims.

What is claimed is:

1. An introducer, comprising:
   a) a sheath comprising a sheath sidewall defining a sheath lumen, the sheath comprising a sheath length extending from a proximal sheath portion having a proximal sheath end to a distal sheath end;
   b) a housing body comprising a housing sidewall extending along a housing length from a proximal housing portion having a proximal housing end to a distal housing portion having a distal housing end, the housing sidewall defining a housing through-bore extending along a longitudinal axis, wherein the housing sidewall has a thickness spaced from the longitudinal axis, and wherein with the distal housing portion secured to the proximal sheath portion, the housing through-bore provides for passage of a medical device through the housing body and into the sheath lumen;
   c) at least one stress confining notch that extends through the entire thickness of the housing sidewall from the proximal housing end partway along the housing length to a stress concentration point spaced from the distal housing end;
   d) a score line having a score line width and a score line length, wherein the score line length extends along a remainder of the housing length of the housing sidewall from the stress concentration point to the distal housing end, wherein the score line width is spaced from and substantially perpendicular to the longitudinal axis, and wherein the notch has a notch width at the proximal housing end that is greater than the score line width; and
   e) wherein the housing is manipulatable to cause a separation force to be applied to the stress concentration point to thereby separate the housing body and the sheath into two generally equal halved along a first plane aligned with the longitudinal axis.

2. The introducer of claim 1 wherein the notch comprises a curved cross section that extends from the proximal housing end to the stress concentration point spaced from the distal housing end.

3. The introducer of claim 1 wherein the notch comprises a rectangular cross section having a notch length extending distally from the proximal housing end, a notch width, and a notch depth, wherein the notch width is greater than the score line width and the notch depth approximates the housing sidewall thickness.

4. The introducer of claim 1 wherein the notch comprises a "v" or wedge-like cross-section comprising a first notch sidewall and a second notch sidewall that converge at the stress concentration point.

5. The introducer of claim 4 wherein the first and second notch sidewalls are angled from about 5° to about 90° at a notch angle measured from the longitudinal axis to a surface of the first or second sidewall.

6. The introducer of claim 1 wherein the housing body has at least two opposing wings which facilitate manipulation to initiate a tear along the housing length beginning at the stress concentration point.

7. The introducer of claim 6 wherein an upper wing surface of each of the two opposing wings meet a proximal housing end surface at respective obtuse angles.

8. The introducer of claim 7 wherein the stress concentration point resides along a second plane aligned normal to the longitudinal axis and wherein the second plane is at a distal location with respect to where the upper wing surfaces meet the proximal housing end surface at the respective obtuse angles.

9. The introducer of claim 1 wherein the housing body is of a material selected from the group consisting of an acrylic polymer, an ethyl acrylate, a 2-chloroethyl vinyl ether, a 2-ethylhexyl acrylate, a hydroxyethyl methacrylate, a butyl acrylate, a butyl methacrylate, and combinations thereof.

10. The introducer of claim 1 wherein the sheath is composed of a fluoropolymeric material selected from the group consisting of PTFE, polyhexafluoropropylene, tetrafluoroethylene-hexafluoropropylene copolymers, tetrafluoroethylene-perfluoroalkyl vinyl ether copolymers, polytrifluoroethylene, ethylene-tetrafluoroethylene copolymers, fluoroethylene-hydrocarbon vinyl ether copolymers, polychlorotrifluoroethylene, ethylene-chlorotrifluoroethylene copolymers, polyvinyl fluoride, polyvinylidene fluoride, vinylidene fluoride-hexafluoropropylene copolymers, fluorinated (meth)acrylate resins, 2-fluoroacrylate resins, fluorinated epoxy resins, fluorinated epoxy (meth)acrylate resins, fluorinated polyether resins, fluorinated polyimide resins, fluorinated polyester resins, fluorinated polyamide resins, fluorinated polycarbonate resins, fluorinated polyformal resins, fluorinated polyketone resins, fluorinated polyazomethine resins, fluorinated polyazole resins, and fluorinated polyallyloxysilane resins, vinylidene fluoride-hexafluoropropylene fluoroelastomer, vinylidene fluoride-tetrafluoroethylene fluoroelastomer, tetrafluoroethylene-perfluoroalkyl vinyl ether fluoroelastomer, vinylidene fluoride-tetrafluoroethylenehexafluoropropylene fluoroelastomer, vinylidene fluoride-tetrafluoroethylene-perfluoroalkyl vinyl ether fluoroelastomer, tetrafluoroethylene-perfluoroalkyl vinyl ether fluoroelastomer, propylene-tetrafluoroethylene fluoroelastomer, fluorosilicone rubber, fluorinated phosphazene rubber, fluorinated thermoplastic rubbers, flexible fluorocarbon resins, and combinations thereof.

11. The introducer of claim 1 wherein the introducer assembly comprises a dilator subassembly, the dilator subassembly comprising an elongated dilator sheath connected to a bulbous dilator head.

12. The introducer of claim 11 wherein a helical thread resides along a dilator head exterior surface threadingly engagable within a corresponding groove residing within an interior surface of a proximal housing portion.

13. The introducer of claim 1 wherein a separation crack is propagatable along a score-line that extends distally from the stress concentration point to the distal housing end.

14. The introducer of claim 1 wherein the housing body has at least two opposing wings which facilitate manipulation to initiate a tear along the length of the housing body beginning at the stress concentration point.

15. An introducer, comprising:
a) a sheath comprising a sheath sidewall defining a sheath lumen, the sheath comprising a sheath length extending from a proximal sheath portion having a proximal sheath end to a distal sheath end;
b) a housing body comprising a housing sidewall extending along a housing length from a proximal housing portion having a proximal housing end to a distal housing portion having a distal housing end, the housing sidewall defining a housing through-bore extending along a longitudinal axis, wherein the housing sidewall has a substantially uniform annular thickness extending from the proximal housing end to the distal housing portion, spaced from the longitudinal axis and wherein with the distal housing portion secured to the proximal portion of the sheath, the housing through-bore provides for passage of a medical device through the housing body and into the sheath lumen;
c) at least one stress confining notch extending through the entire thickness of the housing sidewall from the proximal housing end partway along the housing length to a stress concentration point spaced from the distal housing end;
d) a score line having a score line width and a score line length, wherein the score line length extends along a remainder of the housing length of the housing sidewall from the stress concentration point to the distal housing end, wherein the score line width is spaced from and substantially perpendicular to the longitudinal axis, and wherein the notch has a notch width at the proximal housing end that is greater than the score line width; and
e) wherein the housing is manipulatable to cause a separation force to be applied to the stress concentration point to thereby cause a separation crack to propagatable along a score-line extending distally from the stress concentration point and residing within a portion of the exterior surface of the housing body.

16. The introducer assembly of claim 15 wherein the introducer assembly comprises a dilator subassembly, the dilator subassembly comprising an elongated dilator sheath connected to a bulbous dilator head.

17. The introducer assembly of claim 15 wherein a helical thread resides along a dilator head exterior surface threadingly engagable within a corresponding groove residing within an interior surface of a proximal housing portion.

18. The introducer of claim 15 wherein the housing body has at least two opposing wings which facilitate manipulation to initiate a tear along the length of the housing body beginning at the stress concentration point.

19. The introducer of claim 18 wherein an upper wing surface of each of the two opposing wings meet a proximal housing end surface at respective obtuse angles.

20. The introducer of claim 19 wherein the stress concentration point resides along a second plane aligned normal to the longitudinal, axis and wherein the second plane is at a distal location with respect to where the upper wing surfaces meet the proximal housing end surface at the respective obtuse angles.

* * * * *